United States Patent
Makarov

(10) Patent No.: US 10,043,648 B2
(45) Date of Patent: Aug. 7, 2018

(54) HIGH DUTY CYCLE ION SPECTROMETER

(71) Applicant: Thermo Fisher Scientific (Bremen) GmbH, Bremen (DE)

(72) Inventor: Alexander Alekseevich Makarov, Bremen (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 0 days.

(21) Appl. No.: 15/640,129

(22) Filed: Jun. 30, 2017

(65) Prior Publication Data
US 2017/0301529 A1    Oct. 19, 2017

Related U.S. Application Data

(63) Continuation of application No. 15/075,082, filed on Mar. 18, 2016, now Pat. No. 9,704,696, which is a
(Continued)

(30) Foreign Application Priority Data

Nov. 24, 2011 (GB) .................................. 1120307.2

(51) Int. Cl.
*H01J 49/04* (2006.01)
*H01J 49/00* (2006.01)
(Continued)

(52) U.S. Cl.
CPC .......... *H01J 49/10* (2013.01); *H01J 49/0027* (2013.01); *H01J 49/0031* (2013.01);
(Continued)

(58) Field of Classification Search
USPC ....... 250/281, 282, 283, 285, 286, 287, 288, 250/290, 292, 293, 296
See application file for complete search history.

(56) References Cited

U.S. PATENT DOCUMENTS 5,576,540 A    11/1996  Jolliffe
5,763,878 A    6/1998  Franzen
(Continued)

FOREIGN PATENT DOCUMENTS

CN    101320016 A    12/2008
CN    102224562 A    10/2011
(Continued)

Primary Examiner — Bernard Souw
(74) Attorney, Agent, or Firm — Charles B. Katz

(57) ABSTRACT

An ion spectrometer is provided, comprising: an ion source, arranged to generate ions continuously with a first range of mass to charge ratios; and an ion trap, arranged to receive ions from the ion source along an axis, and to eject ions with a second range of mass to charge ratios orthogonally to that axis, the second range of mass to charge ratios being narrower than the first range of mass to charge ratios. In some embodiments, ions generated by the ion source continuously flow into the ion trap. Additionally or alternatively, ion optics receive ions ejected from the ion trap and cool the ions without substantial fragmentation. An ion analyser receives ions ejected from the ion trap or ion optics and separates the ions in accordance with at least one characteristic of the ions.

14 Claims, 3 Drawing Sheets

Related U.S. Application Data continuation of application No. 14/746,753, filed on Jun. 22, 2015, now Pat. No. 9,293,315, which is a continuation of application No. 14/360,345, filed as application No. PCT/EP2012/073640 on Nov. 26, 2012, now Pat. No. 9,064,679.

(51) Int. Cl.

| | |
|---|---|
| *H01J 49/10* | (2006.01) |
| *H01J 49/40* | (2006.01) |
| *H01J 49/06* | (2006.01) |
| *H01J 49/42* | (2006.01) |
| *G01N 27/62* | (2006.01) |

(52) U.S. Cl.
CPC ......... *H01J 49/0481* (2013.01); *H01J 49/06* (2013.01); *H01J 49/063* (2013.01); *H01J 49/401* (2013.01); *H01J 49/423* (2013.01); *H01J 49/425* (2013.01); *H01J 49/426* (2013.01); *H01J 49/427* (2013.01); *H01J 49/4215* (2013.01); *H01J 49/4295* (2013.01); *G01N 27/622* (2013.01)

(56) References Cited

U.S. PATENT DOCUMENTS

| | | | |
|---|---|---|---|
| 5,783,824 A * | 7/1998 | Baba | .................. H01J 49/423 250/281 |
| 7,157,698 B2 | 1/2007 | Makarov et al. | |
| 7,348,554 B2 | 3/2008 | Hashimoto et al. | |
| 7,893,401 B2 | 2/2011 | Ding | |
| 8,217,344 B2 | 7/2012 | Miller et al. | |
| 8,399,828 B2 | 3/2013 | Vestal | |
| 8,637,816 B1 | 1/2014 | Mordehai et al. | |
| 8,809,769 B2 | 8/2014 | Park | |
| 8,853,622 B2 | 10/2014 | Senko | |
| 8,957,369 B2 | 2/2015 | Makarov | |
| 9,064,679 B2 * | 6/2015 | Makarov | ................. H01J 49/06 |
| 9,293,315 B2 * | 3/2016 | Makarov | ................. H01J 49/06 |
| 9,704,696 B2 * | 7/2017 | Makarov | ................. H01J 49/06 |
| 2003/0155498 A1 * | 8/2003 | Kato | ................... H01J 49/0095 250/281 |
| 2007/0045533 A1 | 3/2007 | Krutchinsky et al. | |
| 2007/0176091 A1 | 8/2007 | Lange et al. | |
| 2008/0185511 A1 | 8/2008 | Senko | |
| 2008/0251712 A1 | 10/2008 | Sanders et al. | |
| 2009/0179150 A1 | 7/2009 | Kovtoun et al. | |
| 2010/0072362 A1 | 3/2010 | Giles et al. | |
| 2010/0108878 A1 | 5/2010 | Bateman et al. | |
| 2010/0243883 A1 | 9/2010 | Vidal-De-Miguel | |
| 2011/0057097 A1 | 3/2011 | Bateman et al. | |
| 2014/0326870 A1 * | 11/2014 | Makarov | ................. H01J 49/06 250/283 |
| 2014/0346345 A1 | 11/2014 | Makarov | |
| 2015/0155147 A1 | 6/2015 | Makarov | |
| 2016/0203962 A1 * | 7/2016 | Makarov | ................. H01J 49/06 250/282 |

FOREIGN PATENT DOCUMENTS

| | | |
|---|---|---|
| GB | 2427067 A | 12/2006 |
| GB | 2449760 A | 12/2008 |
| GB | 2440364 B2 | 2/2010 |

* cited by examiner

HIGH DUTY CYCLE ION SPECTROMETER

CROSS-REFERENCE TO RELATED APPLICATIONS

This application is a continuation under 35 U.S.C. § 120 and claims the priority benefit of co-pending U.S. patent application Ser. No. 15/075,082 filed Mar. 18, 2016, which is a continuation of U.S. patent application Ser. No. 14/746, 753 filed Jun. 22, 2015, now U.S. Pat. No. 9,293,315, which is a continuation of U.S. patent application Ser. No. 14/360, 345 filed May 23, 2014, now U.S. Pat. No. 9,064,679, which is the United States National Stage Application, under 35 USC 371, of International Application No. PCT/EP2012/073640 having an international filing date of Nov. 26, 2012 and designating the United States, which claims priority to GB 1120307.2, filed Nov. 24, 2011, said applications incorporated by reference herein in their entireties.

TECHNICAL FIELD

This invention relates to an ion spectrometer (such as an ion mobility spectrometer) or a mass spectrometer particularly comprising a sequential scanning mass analyzer, such as quadrupole mass filter, magnetic sector, multi-reflection time-of-flight and electrostatic trap mass analyzers.

BACKGROUND TO THE INVENTION

Modern continuous ion sources provide up to $10^9$ ions per second in the case of Electrospray Ionisation (ESI), photoionisation (PI) and Atmospheric Pressure Chemical Ionisation (APCI) sources, up to $10^{10}$ ions per second in the case of Electron Ionisation (EI) sources and up to $10^{11}$ ions per second in the case of Inductively Coupled Plasma (ICP) ion sources. Desirably, for the highest sensitivity and speed of analysis, mass analysis of ions from these ion sources would be achieved, without allowing ions to go to waste, on a continuous basis.

Sequential scanning mass analyzers comprise a mass filter, which transmits ions with only a narrow range of mass to charge ratios at a given time. Hence, such analyzers waste any ions that are not of the mass to charge ratio being transmitted, since these ions are lost.

This means that existing mass spectrometers using such analyzers operate with a low duty cycle (typically between 0.1% and 10%) when performing quantitation analysis where multiple target compounds need to be analysed. The use of continuous ion sources, such as electrospray ionisation sources, may mean that ions are wasted when the analyser duty cycle is so low.

Nevertheless, sequential scanning mass analyzers offer improved linearity and dynamic range over the alternatives. Hence, it is desirable to improve the duty cycle of such mass spectrometers. Similar issues arise in relation to other types of ion spectrometer, such as ion mobility spectrometers or mass spectrometers, in which improvement in the duty cycle may be especially beneficial.

SUMMARY OF THE INVENTION

Against this background, the present invention provides an ion spectrometer, comprising an ion source, arranged to generate ions continuously with a first range of mass to charge ratios; an ion trap, arranged to receive ions from the ion source along an axis, and to eject ions with a second range of mass to charge ratios orthogonally to that axis, the second range of mass to charge ratios being narrower than the first range of mass to charge ratios; a power supply, coupled to the ion source and ion trap so as to provide a potential causing ions generated by the ion source to continuously flow into the ion trap; and an ion analyser, arranged to receive ions ejected from the ion trap and separate the ions in accordance with at least one characteristic of the ions.

The ion source produces a continuous beam of ions having a wide range of mass to charge ratios and is coupled to the ion trap, so that ions from the source enter the ion trap in an uninterrupted stream. Ions of a narrow range of mass to charge ratios are ejected from the ion trap whilst at the same time other ions received by the ion trap may be continuously stored and held ready for future ejection. The ion trap thus acts as a combination of a continuously filled trap and a mass pre-filter.

Hence, ions that are not required by the analyzer are not wasted, but can instead be stored for ejection at a suitable instant. This can also improve the dynamic range of the spectrometer, since the analyzer can be filled to its space charge capacity limit with more ions within the analysis range. This also allows a detection limit to be reached in a shorter space of time.

Moreover, by ejecting ions orthogonally from the ion trap, the ion trap can be closely coupled to the analyzer. This also reduces wastage of ions and improves speed. Together, these advantages allow more ions to be usefully processed in a shorter space of time, such that the spectrometer can achieve a high duty cycle.

The present invention thereby provides effective improvement of the duty cycle close to the number of m/z windows of interest at a given moment. Typically, the duty cycle is improved to between 10% and 20%.

The term "continuous" as used herein can also relate to a quasi-continuous, intermittent or even pulsed ion current, under conditions in which ejection of ions from the trap is not tightly correlated with arrival of ions of a particular m/z ratio to the trap.

Advantageously, the power supply is further arranged to provide an RF potential to the ion trap, so as to cause an electric field having a quasi-potential well in the dimension orthogonal to the axis along which ions with the second range of mass to charge ratios are ejected. As ions are injected into the ion trap, their radial energy is not high enough to escape from the quasi-potential well formed by the RF field. As the ions then cool down during their stay within the trap, their radial energy becomes even lower. Advantageously, the ions are caused to enter the trap by a DC potential between the ion source and the ion trap. In this way, ions can be stored in the ion trap continuously, and at the same time, be selectively ejected from the ion trap according to their mass to charge ratio.

In the preferred embodiment, the spectrometer further comprises: ion optics, arranged to receive ions ejected from the ion trap and cool the ions. Preferably, the ion optics are arranged to cool the ions without substantial fragmentation. Moreover, the ion analyser may then be arranged to receive ions from the ion optics. Placing ion optics to cool the ions between the ion trap and the ion analyser reduces the energy of the ions and allows their accurate analysis.

In a second aspect, the present invention may be found in an ion spectrometer, comprising: an ion source, arranged to generate ions with a first range of mass to charge ratios; an ion trap, arranged to receive ions from the ion source along an axis, and to eject ions with a second range of mass to charge ratios orthogonally to that axis, the second range of mass to charge ratios being narrower than the first range of mass to charge ratios; ion optics, arranged to receive ions ejected from the ion trap and cool the ions without substantial fragmentation; and an ion analyser, arranged to receive ions ejected from the ion optics and separate the ions in accordance with at least one characteristic of the ions.

The use of ion optics as a cooling guide makes this arrangement suitable for simple spectrometry, with a high duty cycle.

The invention is particularly adapted for high space charge density, for instance transferring more than $10^8$ charges per second through the ion trap. The purpose of this may be to improve the effective brightness of the ion source for the downstream analyser. The peak ion current within ions of the second range of mass to charge ratios ejected from the ion trap is at least: 5; 10; or 20 times higher than the average current within the ions of the second range of mass to charge ratios received at the ion trap from the ion source. Additionally or alternatively, the average ion current received by the mass filter may be at least 10 pA.

High space charge density may be achieved in a number of ways. For example, the length of rod electrodes in the traps or ion optics may be chosen to be substantial, such as hundreds of millimetres. Moreover, the inscribed radius of the rod electrodes may be large and the trapping frequency may be high. The effect may further be improved when the ions are scanned out quickly. Additionally, where the mass analyser the resolution of mass selection during scanning may be compromised.

A configuration similar to that of the present invention is shown in commonly assigned patent U.S. Pat. No. 7,157,698. However, this patent concerns tandem mass spectrometry. In that case, ions are ejected from an ion trap to a collision cell, in which at some of the ions are fragmented. It is suggested there, that orthogonal mass-selective ejection in tandem mass spectrometry allows typically much higher ejection efficiencies, much higher scan rates, better control over ion population as well as higher space charge capacity. However, it was not previously understood that these advantages would also be applicable for single mass spectrometry. However, by ejecting ions from the ion trap to ion optics for cooling, similar advantages may be obtained for single mass spectrometry as well, especially when a high space charge density is implemented, as discussed above. In a further embodiment, the ion source may be a continuous ion source and the ion trap receives ions continuously from the ion source along the axis.

A number of optional, preferable and advantageous features can be applicable to either of these two aspects. Some of these are now discussed below.

The invention is especially applicable to spectrometers comprising a mass analyser, mass filter, ion mobility analyser or any combination of these. In some embodiments, the ion analyser comprises (or is) a mass filter or mass analyser. In preferred embodiments, the ion analyser comprises (or is) a sequential scanning mass filter, arranged to receive ions ejected from the ion trap and to transmit ions sequentially according to their mass to charge ratio. Additionally or alternatively, the ion analyser comprises an ion mobility analyser.

Preferably, the ion trap is further arranged to store the received ions and to continue to store any received ions that are not ejected.

In the preferred embodiment, the ion trap comprises a power supply and a plurality of electrodes. The power supply may be arranged to supply to the plurality of electrodes one or more of: a DC potential; an RF potential; and an excitation potential. When the power supply applies the excitation potential to the plurality of electrodes, the power supply may be further arranged such that the excitation potential causes ions with the second range of mass to charge ratios to be ejected from the ion trap. Ejection of the ions by their axial excitation may also assist in allowing continuous filling of the ion trap at the same time. Only ions stored in the ion trap that are in resonance with the field generated by the excitation potential across the electrodes (preferably rods) will acquire radial energy. This energy will grow until they get ejected from the ion trap, overcoming the quasi-potential well generated by the RF field. By changing the frequency of the excitation potential, ions of different mass to charge ratios may be ejected. Preferably, the ion trap comprises a quadrupole ion trap.

In this way, the ions are ejected through the entire length of the electrodes in a 'ribbon' beam. This results in an improved ion ejection energy, which is less dependent on space charge. Moreover, it allows an increase in the space charge capacity of the ion trap without compromising its performance, speed or efficiency of ejection. Such an arrangement is especially advantageous with the high space charge density embodiments discussed above.

Advantageously, the ion optics comprises a collision cooling guide arranged to receive ions from the ion trap. This may comprise a gas and be arranged to cause the ions to collide with the gas so as to cool the ions, and to eject the ions to the ion analyser. Beneficially, the ion trap and collision cooling guide share a common housing. Preferably, the collision cooling guide comprises an RF ion guide. Ions are then still efficiently cooled during their travel, thus being prepared for injection into a mass analyser or ion mobility analyser. Hence, the present invention may represent a fusion of quadrupole and linear trap technologies.

Preferably, the ion trap comprises an exit slit and the collision cooling guide comprises an entrance slit. The exit slit of the ion trap may then advantageously be located adjacent the entrance slit of the collision cooling guide.

The ion optics (in the preferred embodiment, a collision cooling guide) are preferably arranged to receive ions from the ion trap along a primary axis and to eject ions along a secondary axis, the secondary axis being substantially orthogonal to the primary axis. Optionally, the secondary axis of the collision cooling guide may be parallel with the axis of the ion trap.

Where the collision cooling guide is an RF ion guide, this RF ion guide may comprise a power supply and a plurality of electrodes. Then, the power supply may be arranged to supply DC potentials to the plurality of electrodes such that a potential well is generated along the primary axis. This causes the ions to be trapped in the collision cooling guide for effective cooling.

According to another aspect, the present invention may be found in a method of ion spectrometry, comprising: generating ions continuously in an ion source with a first range of mass to charge ratios; receiving ions continuously from the ion source at an ion trap along an axis; ejecting ions with a second range of mass to charge ratios from the ion trap orthogonally to that axis, the second range of mass to charge ratios being narrower than the first range of mass to charge ratios; receiving ions ejected from the ion trap at an ion analyser.

Advantageously, the method further comprises storing ions received at the ion trap along the axis, by providing an RF potential to the ion trap, so as to cause an electric field having a quasi-potential well in the dimension orthogonal to the axis along which ions with the second range of mass to charge ratios are ejected.

In the preferred embodiment, the method further comprises: receiving ions ejected from the ion trap at ion optics; cooling ions received at the ion optics; and ejecting the cooled ions to the ion analyser. Preferably, the step of cooling ions is performed without substantial fragmentation of the ions.

In a yet further aspect, the invention may be found in a method of mass spectrometry, comprising: generating ions in an ion source with a first range of mass to charge ratios; receiving ions from the ion source at an ion trap along an axis; ejecting ions with a second range of mass to charge ratios from the ion trap orthogonally to that axis, the second range of mass to charge ratios being narrower than the first range of mass to charge ratios; receiving ions ejected from the ion trap at ion optics; cooling ions received at the ion optics without substantial fragmentation; ejecting the cooled ions to an ion analyser; and receiving ions ejected from the ion optics at the ion analyser.

A number of optional, preferable and advantageous features can be applicable to either of these two method aspects. Some of these are now discussed below.

In some embodiments, the ion analyser comprises (or is) a mass filter. Preferably, the ion analyser comprises (or is) a sequential scanning mass filter. Then, the method may further comprise ejecting ions sequentially according to their mass to charge ratio from the sequential scanning mass filter. Additionally or alternatively, the ion analyser comprises (or is) an ion mobility analyser.

Optionally, the ion optics may comprise a collision cooling guide, comprising a gas. Then, the step of cooling the ions may comprise causing the ions to collide with the gas so as to cool the ions. In some embodiments, the ion trap and collision cooling guide may share a common housing. Preferably, the collision cooling guide comprises an RF ion guide. More preferably, the ion trap comprises an exit slit and the collision cooling guide comprises an entrance slit and the exit slit of the ion trap is located adjacent the entrance slit of the collision cooling guide.

In the preferred embodiment, the step of receiving ions at the ion optics from ion trap takes place along a primary axis and the step of ejecting ions from the ion optics takes place along a secondary axis. Advantageously, the secondary axis is orthogonal to the primary axis. Beneficially, the secondary axis along which the ions are ejected from the ion optics is parallel with the axis of the ion trap along which ions are received from the ion source.

In embodiments where the ion optics comprises an RF ion guide, the step of receiving ions at the ion optics optionally comprises applying DC potentials to a plurality of electrodes of the RF ion guide such that a potential well is generated along the primary axis.

In some embodiments, the peak ion current within ions of the second range of mass to charge ratios ejected from the ion trap is at least: 5; 10; or 20 times higher than the average current within the ions of the second range of mass to charge ratios received at the ion trap from the ion source. Additionally or alternatively, the average ion current received by the ion analyser is at least 10 pA.

Preferably, the method also comprises: storing the ions received at the ion trap; and continuing to store any ions received at the ion trap that are not ejected from the ion trap. Optionally, the number of ions within second range of mass to charge ratios is no more than 10% of the number of ions within the first range of mass to charge ratios.

As used herein, ejection orthogonal to the axis of the ion trap is to be understood to mean ejection which comprises a range of ejection angles largely centred upon an angle orthogonal to the axis of the ion trap. The axis of the ion trap is preferably straight, but may be curved. In embodiments in which the axis of the ion trap is curved, ejection at each point along the axis of the ion trap is largely centred upon an angle orthogonal to the local axis of the ion trap at that point. The ejection angle is largely centred upon an angle orthogonal to the ion trap but the presence of the potential between the ion source and the ion trap which facilitates continuous filling of the ion trap may introduce an offset angle, for example.

A curved axis may provide the benefit of accelerated transfer of ions from the cooling guide towards a quadrupole mass filter or other device. The offset angle might also appear as the result of any remaining axial energy, especially at low gas pressure, or the focusing action of ion optics during transfer.

It will also be understood that the present invention is not limited to the specific combinations of features explicitly disclosed, but also any combination of features that are described independently and which the skilled person could implement together.

BRIEF DESCRIPTION OF THE DRAWINGS

The invention may be put into practice in various ways, one of which will now be described by way of example only and with reference to the accompanying drawings in which.

SPECIFIC DESCRIPTION OF A PREFERRED EMBODIMENT

Figure 1:
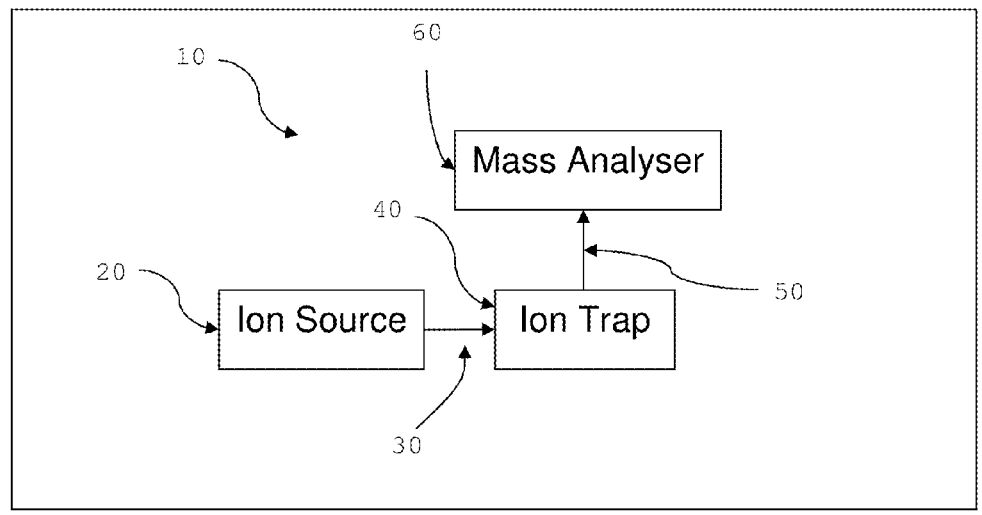
FIG. 1 shows a schematic diagram illustrating a first embodiment of the present invention.

Referring first to FIG. 1, there is shown a schematic diagram illustrating a first embodiment of the present invention.

A mass spectrometer 10 comprises an ion source 20; an ion trap 40; and a sequential scanning mass analyser 60. The ion source 20 generates ions 30 continuously with a first range of mass to charge ratios. The ion trap 40 receives ions 30 continuously with the first range of mass to charge ratios and orthogonally ejects ions 50 with a second range of mass to charge ratios. The second range of mass to charge ratios is narrower than the first range of mass to charge ratios. The ions 50 are then received by the sequential scanning mass analyser 60 for analysis.

Figure 2:
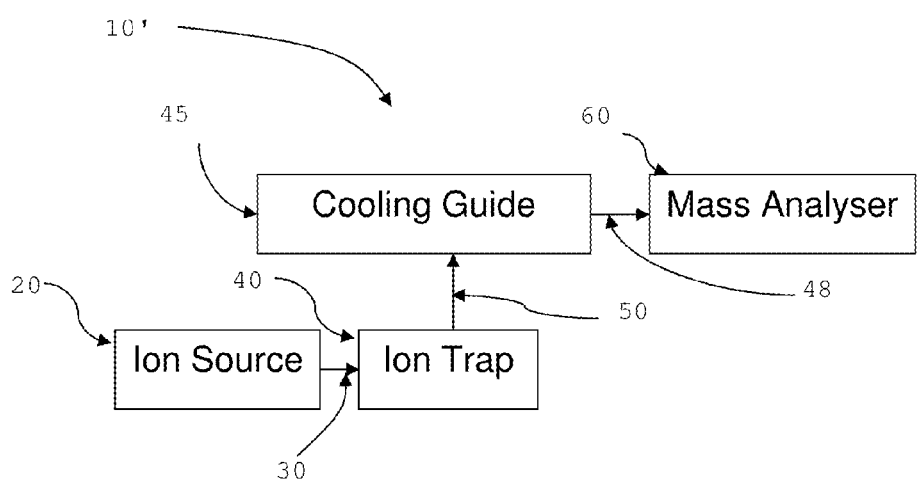
FIG. 2 shows a schematic diagram illustrating a second embodiment of the present invention.

Referring next to FIG. 2, there is shown a schematic diagram illustrating a second embodiment of the present invention.

A mass spectrometer 10' comprises an ion source 20; an ion trap 40; a cooling guide 45 and a sequential scanning mass analyser 60. The ion source 20 generates ions 30 with a first range of mass to charge ratios. The ion trap 40 receives ions 30 with the first range of mass to charge ratios and orthogonally ejects ions 50 with a second range of mass to charge ratios to the cooling guide 45. The second range of mass to charge ratios is narrower than the first range of mass to charge ratios. The cooling guide 45 cools the received ions 50, without substantial fragmentation. The energy of the ions is typically reduced to a few eV or even to less than 1 eV. Cooled ions 48 are ejected axially to the sequential scanning mass analyser 60 for analysis.

Figure 3:
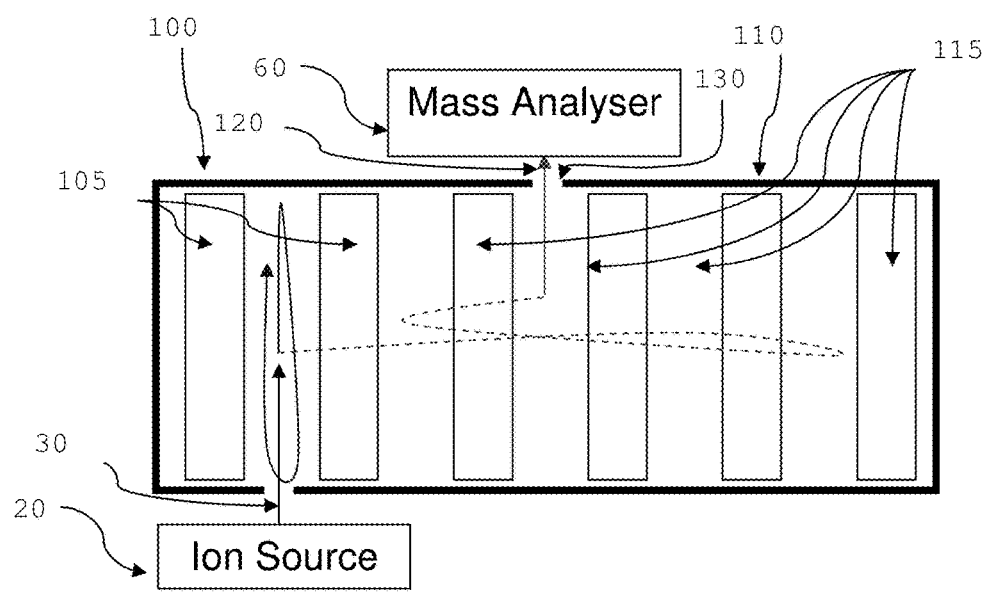
FIG. 3 shows a top view of an embodiment of the present invention according to the schematic diagrams of FIGS. 1 and 2.

Referring now to FIG. 3, there is shown a top view of an embodiment of the present invention according to the schematic diagrams of FIG. 1 and FIG. 2. Where components identical to those in FIG. 1 are shown, the same reference numbers are used.

Ion source 20 ejects ions 30 with a first range of mass to charge ratios. Quadrupole ion trap 100 receives ions 30, and orthogonally ejects ions 50, with a second range of mass to charge ratios, to collision cooling guide 110. Cooled ions 120 are ejected from collision cooling guide 110 to mass analyser 60.

Ions 30 continuously enter quadrupole ion trap 100 from ion source 20. This is effected by a DC potential gradient between the ion source 20 and the entrance to the ion trap 100. Quadrupole ion trap 100 is gas-filled and comprises rods 105. The potentials on the rods cause ions 50, with a second range of mass to charge ratios, to be ejected to collision cooling guide 110. Collision cooling guide 110 comprises rods 115. The potentials on the rods cause ions 120 to be axially ejected to mass analyser 60.

Figure 4:
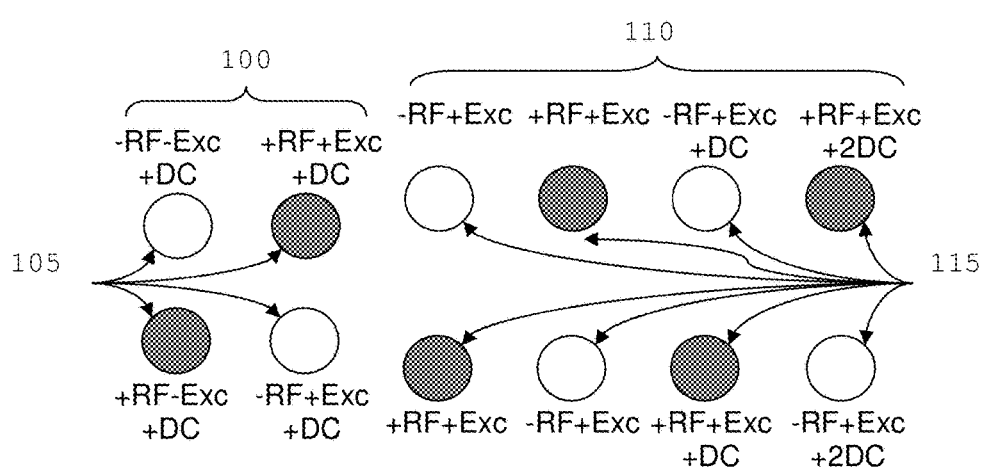
FIG. 4 shows a side view of the embodiment of FIG. 3.

FIG. 4, which shows a side view of the embodiment of FIG. 2, provides more information on how the potentials on rods 105 and rods 115 are configured.

Quadrupole ion trap 100 acts as an excitation guide. Rods 105 are provided with DC and RF potentials, which cause an electric trapping field that holds received ions 30. This causes a quasi-potential barrier separating ions 30 from the adjacent collisional cooling guide 110.

As ions are injected into the quadrupole ion trap 100, their radial energy is not high enough to escape from the quasi-potential barrier formed by the RF potentials. As the ions cool down, their radial energy becomes even lower. Thus, the ions become trapped in the ion trap 100.

Rods 105 are also provided with an excitation potential. The excitation potential causes rapid low-quality resonant excitation such that only ions with a certain mass to charge ratio (m/z) sub-range acquire radial energy sufficient to overcome the quasi-potential barrier and are thereby ejected orthogonally from the trap through an exit slit. By changing the frequency of excitation, ions of different m/z may be ejected. This may operate in a similar way to the quadrupole ion trap described in commonly assigned patent, U.S. Pat. No. 7,157,698. However, due to the application of DC potentials between the ion source 20 and ion trap 100 as explained above, ions continue to enter the trap even during this ejection process. This continuous injection advantageously operates in combination with orthogonal ejection of a selected subset of the ions.

Figure 5:
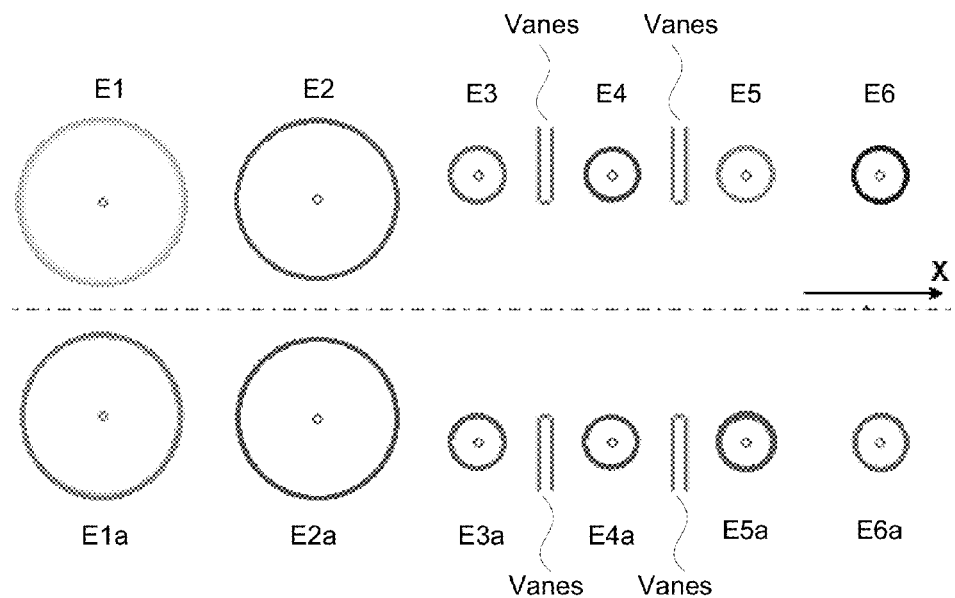
FIG. 5 shows the side view of FIG. 4 for an alternative embodiment of the invention.
Figure 6:
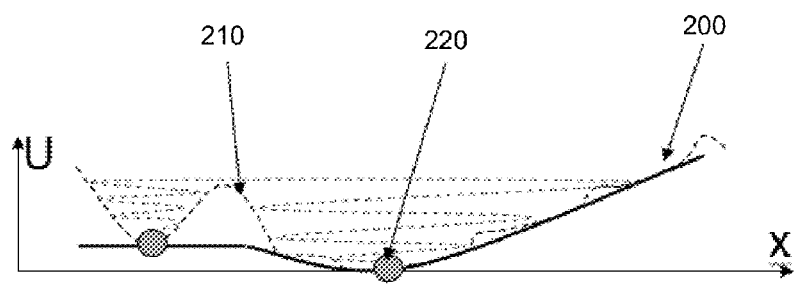
FIG. 6 shows a plot of potential against distance for the embodiment of FIGS. 3, 4 and 5, operating in a high duty cycle mode.

This is illustrated in FIG. 6, which shows a plot of potential against distance for the embodiment of FIGS. 3, 4 and 5, operating in a high duty cycle mode. Curve 200 shows the DC potentials in the direction transverse to rods 105. Curve 210 shows the quasi-potential barrier. Typically, only 5%-10% of the total mass range is orthogonally ejected in this way.

Ions remaining in the quadrupole ion trap 100 are cooled and stored until their turn or until all ions are purged, for instance by reducing the RF potential, or by removal of the DC barrier in the cooling guide 110.

The RF-pseudo-potential is proportional to the square of the RF amplitude. If the amplitude is increased twofold, the RF pseudo-potential well appears to be four times deeper, when the RF frequency is fixed. Thus, the AC amplitude should be increased by a factor of four and the AC frequency by factor of two.

Returning again to FIG. 3, the collisional cooling guide 110 is gas-filled and has a large width and comprises rods 115. Ions enter the guide 110 from the quadrupole ion trap 100 in the direction transverse to rods 115. Rods 115 are provided with a retarding DC field in this transverse direction to allow sufficient length of travel of the ions on entry to the guide 110. The collisional cooling guide 110 is provided with an exit 130.

Collisions with gas over this substantial length dampen the ion energy and they relax to the bottom of a DC potential well 220, which is illustrated in FIG. 6. This well is aligned to the exit from the cooling guide 130. This allows ions 120 to leave this guide into mass analyser 60.

In such an embodiment, the total time for excitation and transfer between source 20 and mass analyser 60 is not more than few ms. The dwell time in mass analyser is also less than 1 to 3 ms. The gas pressure in the collision cooling guide 110 is between 0.001 and 0.01 mbar. The pressure multiplied by length is between 0.03 and 0.5 mbar*mm The gas in the collisional cooling guide 110 is preferably one or more of: helium, nitrogen, argon. Rods 105 and rod 115 are preferably round in section or generally round in section with hyperbolic profile towards the axis and a diameter of between 1.5 to 3 mm. The distance between the centres of adjacent rods 105 in quadrupole ion trap 100 is between 1.3 to 2 times their diameter. The distance between the centres of adjacent rods 105 in collisional cooling guide 110 is between 1.5 to 3 times the distance between adjacent rods in quadrupole ion trap 100. Some or all of the six pairs of rods shown in FIG. 3 may be sectioned.

The mass resolving power of the quadrupole ion trap 100 is between 10 and 20. This is lower than that of the mass analyser 60. The total cycle time for covering the entire mass range is between 30 to 50 ms. Hence, space charge does not affect the excitation process beyond usability.

The lengths of the excitation guide 100 and collisional cooling guide 110 are 30 to 100 mm. This provides a balance between the desire to maximize space-charge capacity whilst achieving improved speed of ion transfer to the mass analyser.

Referring now to FIG. 5, there is shown the side view of FIG. 4 for an alternative embodiment of the invention. Vanes are also introduced into the cooling guide. For this embodiment, the electrode voltages in full transition mode may be as follows.

|       | E1  | E1a  | E2   | E2a | E3  | E3a  | E4   | E4a | E5  | E5a  | E6   | E6a |
|-------|-----|------|------|-----|-----|------|------|-----|-----|------|------|-----|
| RF, V | 150 | −150 | −150 | 150 | 700 | −700 | −700 | 700 | 700 | −700 | −700 | 700 |
| DC, V | 13  | 4    | 4    | 13  | 3.6 | 3.6  | −3   | −3  | 3   | 3    | 6    | 6   |

Whilst a specific embodiment has been described, the skilled person may contemplate various modifications and substitutions. For instance, axial movement of ions along the cooling guide 110 and transfer into mass filter could be accelerated by any known means of creating axial field, for example, resistive rods or vanes.

The embodiment described above relates to the use of a sequential scanning mass analyser, but it will be appreciated that other types of mass filters or mass analysers may be used. The invention may also be used in conjunction with an ion mobility analyser, in which case this would replace the sequential scanning mass analyser 60 in the arrangement discussed above. Most preferable designs of ion mobility analyser are described in US-2010/243883, GB-2486584, GB-2382919.

Further detection systems may also be provided. These may be used in the combination where the analyser part of the arrangement (that is, downstream from the ion trap 40 or cooling guide 45) comprises: an ion mobility analyzer followed by a time-of-flight mass analyser; a mass filter followed by a time-of-flight mass analyser; an ion mobility analyzer or a mass filter followed by an ion trap or a fragmentation cell followed by an analyser, such as a followed by a time-of-flight mass analyser or orbital trapping mass analyser, such as that marketed by Thermo Fisher Scientific under the brand name Orbitrap™; and other similar combinations.

In some configurations, resonant excitation in the ion trap 40 may be achieved by a first RF potential and an auxiliary RF potential. Adding a second (or more than one) RF potential may allow the simultaneous selection (by resonant excitation) of ions of multiple masses or mass ranges, based on the RF potentials applied.

The system could have also other preceding separations which may change a composition of the ion current coming into it, such as mass analysers (for instance, quadrupole, time-of-flight, magnetic sector, etc.) or ion mobility analysers of any type (e.g. field-asymmetric, differential, drift tube, running wave(s), rotating-field, gas flow assisted, etc.). For example, the invention can be used in a tandem quadrupole mass spectrometer, located upstream from a first quadrupole analyser or a collision cell such as a travelling wave (T-Wave) collision cell. It may further be appreciated that the invention may be applicable to a quadrupole time-of-flight (QTOF) mass spectrometer, for instance upstream or in place of a first quadrupole mass analyser. Then, the downstream devices, which may comprise a quadrupole (that is known to be a sequential scanning mass filter) or a travelling wave collision cell (which can be used as a sequentially scanning ion mobility analyzer) acting as real sequential scanning devices. Alternatively, a time-of-flight mass analyser may be located downstream of the invention, which may be so fast so as to have similar properties as a quadrupole mass filter. The invention could also be used between a MALDI source and an ion mobility cell of an ion instrument, such as described in WO-2010/085720 and in particular as shown in FIG. 1 of this document, especially when the MALDI "shot" frequency is high compared with the mass ejection rate of the ion trap of our description. This might be understood as a continuously firing laser, as suggested above. Ion-molecule and ion-ion reactions, collisions with gas, irradiation by photons could also be used, for example, to affect a composition of the ion current.

What is claimed is:

1. A mass spectrometry method, comprising:
   continuously generating ions at an ion source, the ions having a first range of mass-to-charge ratios (m/z's);
   receiving the ions at an ion trap along a first axis;
   ejecting ions with a second range of m/z's from the ion trap to a gas-filled collisional cooling guide along a second axis substantially orthogonal to the first axis while continuing to store the non-ejected ions;
   cooling the ions in the collisional cooling guide without substantial fragmentation; and
   ejecting the cooled ions to a mass analyzer;
   wherein a pressure P within the collisional cooling guide satisfies at least one of the following conditions: (i) P is between 0.001 mbar and 0.01 mbar, or (ii) P*L is between 0.03 mbar*mm and 0.5 mbar*mm, where L is the length of the collisional cooling guide.

2. The method of claim 1, wherein the ion trap continues to receive ions from the ion source while ejecting ions to the collisional cooling cell.

3. The method of claim 1, wherein P is between 0.001 mbar and 0.01 mbar.

4. The method of claim 1, wherein P*L is between 0.03 mbar*mm and 0.5 mbar*mm.

5. The method of claim 1, wherein the second range of m/z's is between 5-10 percent of the first range of m/z's.

6. The method of claim 1, wherein the aggregate time of transfer of ions from the ion source to the mass analyzer is no greater than a few ms.

7. A mass spectrometer, comprising:
   an ion source configured to continuously generate ions having a first range of mass-to-charge ratios (m/z's);
   an ion trap having a plurality of electrodes positioned to receive the ions from the ion source along a first axis, the ion trap being configured to eject a subset of the ions having a second range of m/z's narrower than the first range of m/z's to a collisional cooling guide along a second axis substantially orthogonal to the first axis, the collisional cooling guide being positioned adjacent to the ion trap and having a length L, the ion trap being further configured to continue to store the non-ejected ions;
   the collisional cooling guide being configured to cool ions received from the ion trap and to eject the cooled ions; and
   a mass analyzer positioned to receive the cooled ions from the collisional cooling guide;
   wherein, during operation of the mass spectrometer, the collisional cooling guide is filled with gas to a pressure P that satisfies at least one of the following conditions: (i) P is between 0.001 mbar and 0.01 mbar, or (ii) P*L is between 0.03 mbar*mm and 0.5 mbar*mm.

8. The mass spectrometer of claim 7, wherein P is between 0.001 mbar and 0.01 mbar.

9. The mass spectrometer of claim 7, wherein P*L is between 0.03 mbar*mm and 0.5 mbar*mm.

10. The mass spectrometer of claim 7, wherein the ion trap and the collisional cooling guide each comprise a plurality of rod electrodes oriented in generally parallel relation.

11. The mass spectrometer of claim 10, wherein the rod electrodes have round cross-sections.

12. The mass spectrometer of claim 10, wherein the spacing between adjacent rod electrodes in the collisional cooling guide is between 1.5 to 3 times the spacing between adjacent rod electrodes in the ion trap.

13. The mass spectrometer of claim 7, wherein the lengths of the ion trap and the collisional cooling guide are both in the range of 30 to 100 mm.

14. The mass spectrometer of claim 10, wherein the collisional cooling guide further comprises a plurality of vane electrodes positioned between adjacent rod electrodes.

\* \* \* \* \*